United States Patent [19]

Rowsell et al.

[11] 4,318,900
[45] Mar. 9, 1982

[54] ALICYCLIC AMIDES HAVING A PHYSIOLOGICAL COOLING EFFECT

[75] Inventors: David G. Rowsell, Staines; David J. Spring, Slough; Roger Hems, Maidenhead, all of England

[73] Assignee: Wilkinson Sword Limited, London, England

[21] Appl. No.: 177,359

[22] Filed: Aug. 11, 1980

Related U.S. Application Data

[62] Division of Ser. No. 530,721, Dec. 9, 1974, Pat. No. 4,248,859.

[30] Foreign Application Priority Data

Dec. 12, 1973 [GB] United Kingdom ............... 57528/73

[51] Int. Cl.$^3$ .............................................. A61K 7/22
[52] U.S. Cl. ...................................... 424/54; 131/276; 131/335; 252/110; 252/522 R; 424/45; 424/48; 424/73; 424/156; 424/248.54; 424/267; 424/274; 426/590; 426/660
[58] Field of Search ................. 424/54, 248.54, 267, 424/274; 131/17 R; 426/590

[56] References Cited

U.S. PATENT DOCUMENTS 2,001,046  5/1935  Welch ................................ 424/343
3,511,914  5/1970  Wolkoff et al. .................... 424/343
3,644,653  2/1972  Toheitcheff ........................ 424/358

FOREIGN PATENT DOCUMENTS 2202535  6/1972  Fed. Rep. of Germany .
2205255  6/1972  Fed. Rep. of Germany .

OTHER PUBLICATIONS

Remington's Pharmaceutical Science, 13th Ed (1965), p. 855.
Wilson et al., Textbook of Organic Medicinal and Pharamceutical Chemistry, 4th Ed. (1962), pp. 111–112.
Chemical Abstracts, 7th Coll. Index (1962–1966) pp. 13780 e–13782S.
Chemical Abstracts 8th Coll. Index (1967–1971); pp. 18623s–18627s.
Chemical Abstracts 66:2275z (1967).
Chemical Abstracts 67:53774v (1967).

*Primary Examiner*—Leonard Schenkman
*Attorney, Agent, or Firm*—Leydig, Voit, Osann, Mayer & Holt, Ltd.

[57] ABSTRACT

Alkyl-substituted alicyclic carboxylic acids, esters and amides are disclosed having the property of stimulating the cold receptors of the nervous system of the human body to produce a cold sensation and are used for this purpose in a variety of edible and topical preparations.

15 Claims, No Drawings

ALICYCLIC AMIDES HAVING A PHYSIOLOGICAL COOLING EFFECT

This is a division of application Ser. No. 530,721, filed Dec. 9, 1974, now U.S. Pat. No. 4,248,859.

FIELD OF INVENTION

This invention relates to compositions and compounds having a physiological cooling effect on the skin and on the mucous membranes of the body, particularly those of the mouth, nose, throat and gastrointestinal tract.

BACKGROUND OF THE INVENTION AND PRIOR ART

Menthol is well known for its physiological cooling effect on the skin and mucous membranes of the mouth and has been extensively used as a flavouring agent (menthol being a major constituent of oil of peppermint) in foodstuffs, beverages, dentifrices, mouthwashes, etc. and as a component in a wide range of toiletries, liniments and lotions for topical application. Menthol is also a well known tobacco additive for producing a 'cool' sensation in the mouth when smoking.

It is well established that the "cooling" effect of menthol is a physiological effect due to the direct action of menthol on the nerve endings of the human body responsible for the detection of hot or cold and is not due to latent heat of evaporation. It is believed that the menthol acts as a direct stimulus on the cold receptors at the nerve endings which in turn stimulate the central nervous system.

Although menthol is well established as a physiological coolant its use, in some compositions, is circumscribed by its strong minty odour and its relative volatility.

A few other compounds have been reported in the technical literature as having an odour or flavour similar to menthol and from time to time have been proposed as flavourants or odourants in a variety of topical and ingestible compositions. For example, Japanese Patent Publication No. 39-19627 reports that 3-hydroxymethyl-p-methane (menthyl carbinol) has a flavour closely resembling that of l-menthol and suggests its use as a flavourant in confectionery, chewing gum and tobacco. In Swiss Pat. No. 484,032 certain saccharide esters of menthol are proposed as additives to tobacco. In French Patent Specification No. 1,572,332 N,N-dimethyl 2-ethylbutanamide is reported as having a minty odour and refreshing effect, and the minty odor of N,N-diethyl 2,2-dimethylpropanamide is also referred to. A similar effect is reported for N,N-diethyl 2-ethylbutanamide in Berichte 39, 1223, (1906). A minty odour has also been reported for 2,4,6-trimethylheptan-4-ol and 2,4,6-trimethyl-hept-2-en-4-ol in Parfums-Cosmetiques-Savons, May 1956, pp. 17–20. The cooling effect of menthol and other related terpene alcohols and their derivatives has also been studied and reported in Koryo, 95, (1970), pp. 39–43. 2,3-p-menthane-diol has also been reported as having a sharp cooling taste (Beilstein, Handbuch der Organischen Chemie, 4th Ed. (1923) Vol. 6, p. 744.). Still other substituted p-menthanes having a physiological cooling effect are disclosed in German Offenlegungsschrift Nos. P 22 02 535, P 22 03 947, P 22 03 273 and P 22 05 255.

Despite this knowledge of other compounds having an odour and flavour similar to that of menthol, menthol is still extensively used in topical, ingestible and other compositions notwithstanding the disadvantages mentioned above, namely its very strong odour and its relative volatility.

OBJECTS OF THE INVENTION

It is an object of the present invention to provide other compounds having a pronounced physiological cooling effect, in many cases more persistent than that obtained with menthol, without the attendant disadvantages of a strong minty odour.

It is a further object to provide compounds having a pronounced physiological cooling effect and being of relatively low volatility.

It is a further object of the present invention to provide ingestible, topical and other compositions capable of stimulating the cold receptors of the nervous system of the human body thereby to create a desirable 'cool' sensation, and a method of making them.

It is a yet further object of the present invention to provide a method of stimulating the cold receptors of the nervous system of the body to create a cool sensation.

Other objects will be apparent from the following detailed description of the invention.

SUMMARY OF INVENTION

The present invention is based on the discovery of a group of alkyl-substituted alicyclic carboxylic acids, esters and amides which have a pronounced physiological cooling activity, but which are without the strong minty odour characteristic of menthol and which are of relatively low volatility and which are substantially non-toxic. These compounds are alicyclic carboxylic acids, esters and amides of the formula:

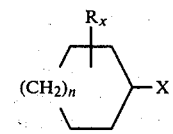

Where
n is 0 or an integer of from 2–6 inclusive;
x has a value of 1, 2 or 3;
R is $C_1$–$C_5$ alkyl, at least one R group being in a 1,2 or 3-position relative to X and the total number of carbon atoms provided by the R groups and the carbocycle to which they are attached being from 8–14, preferably 8–12; and
X is —COOH, COOR', CONR"R''', where R' is $C_2$–$C_4$ hydroxyalkyl;
R", when taken separately, is H or $C_1$–$C_{10}$ alkyl;
R''', when taken separately, is H, $C_1$–$C_{10}$ alkyl or hydroxyalkyl, or alkylcarboxyalkyl of up to 8 carbon atoms, with the proviso that when R" is H, R''' may also be cycloalkyl of up to 8 carbon atoms, phenyl or substituted phenyl containing alkyl, hydroxy or methoxy substituents and a total of up to 10 carbon atoms; and R" and R''', when taken together, represent an alkylene group of up to 8 carbon atoms, the carbon atom chain of which may optionally be interrupted by an oxygen atom.

Preferred compounds usable according to this invention are of formula II:

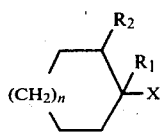

where
n is 0, 2 or 3;
one of $R_1$ and $R_2$ is $C_1$-$C_5$ alkyl and the other is H or $C_1$-$C_5$ alkyl;
X is COOH, COOR', $CONR'^vR^v$ where R' is $C_2$-$C_4$ hydroxyalkyl;
$R'^v$, when taken separately is, H or $C_1$-$C_5$ alkyl;
$R^v$, when taken separately is H, $C_1$-$C_5$ alkyl or hydroxyalkyl, alkylcarboxyalkyl of up to 6 carbon atoms or, when $R'^v$ is H, $C_5$-$C_6$ cycloalkyl, phenyl or phenyl containing methyl, methoxy or hydroxy substituents; and $R'^v$ and $R^v$, when taken together, represent an alkylene group of up to 8 carbon atoms, the carbon atom chain of which may optionally be interrupted by an oxygen atom.

More particularly preferred are compounds of formula II, where one of $R_1$ and $R_2$ is a branched chain alkyl group, preferably with branching in an α-position relative to the ring, and especially an isopropyl or sec-butyl group.

STATEMENT OF INVENTION

In accordance with this invention, therefore, there are provided consumer products for application to or consumption by the human being comprising a consumer product base and a means for stimulating the cold receptors of the nervous system of the human body wherein said means comprise an effective amount of one or more alicyclic carboxylic acids, esters or amides of the formula hereinbefore set forth.

By consumer product we mean a manufactured product applied to or consumed by the human person for toilet, cosmetic, hygienic, nutritive, curative, prophylactic, or other purposes and constituting a vehicle by means of which the said carboxylic acids, esters and amides may be brought into contact with the skin, mucous membranes or other surface tissues of the body, whether external tissues or internal, for example, of the nose, throat, mouth and gastrointestinal tract, and includes liquid and solid phase preparations of an essentially formless nature e.g. solutions, emulsions, pastes, ointments, powders etc., solid phase preparations of semi-permanent form: e.g. shaped toilet and cosmetic preparations and shaped edible preparations, whose shaped form is only temporary and which lose that form on use, and articles of permanent form but which are of an essentially disposable nature, e.g. cleansing tissues, toothpicks etc.

Typical consumer products into which the alicyclic carboxylic acids, esters and amides may be incorporated in accordance with this invention and which may therefore serve as vehicles for application of the compounds to the person are:

1. Edible and potable compositions including alcoholic and non-alcoholic beverages; confectionary; chewing gum; cachous; ice cream; jellies;
2. Toiletries including after-shave lotions, shaving soaps, creams and foams, toilet water, deodorants and antiperspirants, 'solid colognes', toilet soaps, bath oils and salts, shampoos, hair oils, talcum powders, face creams, hand creams, sunburn lotions, cleansing tissues, dentifrices, toothpicks, hair tonics, mouthwashes, eyedrops;
3. Medicaments including antiseptic ointments, pile ointments, liniments, lotions, decongestants, counter-irritants, cough mixtures, throat losenges, antacid and indigestion preparations, and analgesics;
4. Miscellaneous compositions such as water soluble adhesive compositions for envelopes, postage stamps, adhesive labels etc.

DETAILED DESCRIPTION

The acids, esters and amides used in accordance with this invention may be prepared by procedures well known in the art from appropriate starting materials. The following methods are exemplary for the preparation of the acids, which can then be converted to esters and amides by routine procedures, e.g. by conversion to the corresponding acid chloride and subsequent reaction with an appropriate alcohol, amine or ammonia.

(i) Alkylation of nitriles:

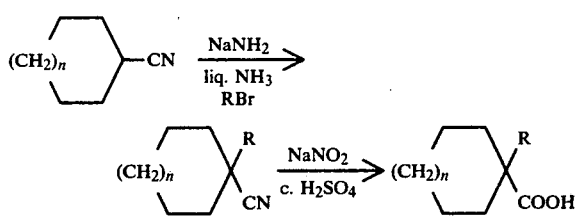

e.g. Tilford et al., J.A.C.S. (1949), 71, 1705.

(ii) Alkylation of a ketone Schiff's base:

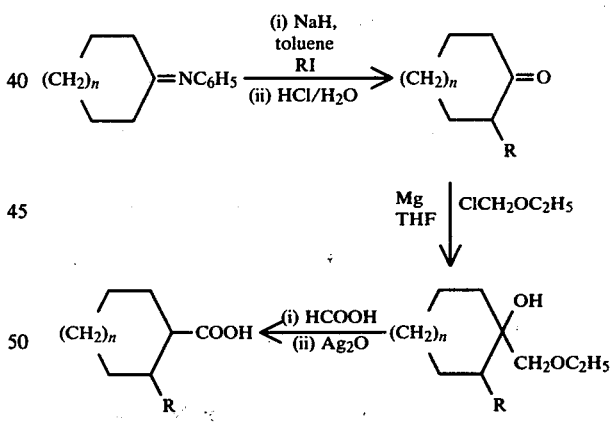

e.g. Stork et al. J.A.C.S. (1963), 85, 2178 and de Botton Compt. Rendu. (1963), 256, 2186.

(iii) Alkylation of ketoesters

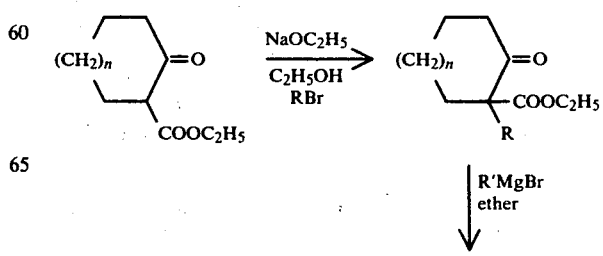

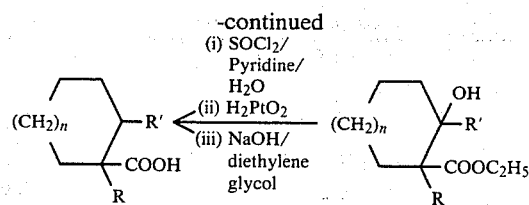

e.g. Shire et al. J.A.C.S. (1941), 63, 2984.

Many of the compounds used as cold receptor stimulants in accordance with this invention exhibit either geometric or optical isomerism or both and, depending on the starting materials and the methods used in their preparation, the compounds may be isomerically pure, i.e. consisting of one geometric or optical isomer, or they may be isomeric mixtures, both in the geometric and optical sense. Generally, the compounds will be used as isomeric mixtures, but in some cases the cooling effect may differ as between geometric or optical isomers, and therefore one or other isomer may be preferred.

For the purposes of the present disclosure the following test procedure has been devised as a means to identify compounds having a physiological cooling activity in accordance with the present invention and herein referred to as cold receptor stimulants. This test is intended purely as a means for identifying compounds having a physiological cooling activity and useful in the present invention and for giving an indication of the different relative activities of the compounds, as between themselves and as compared with menthol, when applied in a particular manner to a particular part of the body. The results are not necessarily indicative of the activity of these compounds in other formulations and other parts of the body where other factors come into play. For example, a controlling factor in the onset of cooling effect, its intensity and longevity will be the rate of penetration of the compounds through the epidermis and this will vary in different locations on the human body. The formulation of actual products according to this invention will therefore be done largely on an empirical basis although the test results and other figures given herein will be useful as a guide, particularly in the formulation of products for oral administration, since the test procedure to be described involves oral application of the compound. A similar test may, of course, be devised for the purpose of measuring the relative activities of the compounds on another area of the body, for example, the face or forearm, and this will be a useful guide in the choice of compounds to be used in preparations for external topical usage.

It will also be noted that the described test procedure is done on a statistical basis. This is necessary since sensitivity to these compounds will vary not only from compound to compound and from one part of the body to another, but also from one individual to another. Tests of this nature are commonly used in the testing of the organoleptic properties, e.g. taste, smell etc., of organic and inorganic compounds, see Kirk-Othmer: Encyclopedia of Chemical Technology, 2nd Ed. (1967) Vol. 14 pages 336–344.

Test Procedure

The following test procedure is aimed at determining the minimum quantity of the test compound required to produce a noticeable cooling effect on a person of average sensitivity, this minimum quantity being termed the threshold for that particular compound. The tests are carried out on a selected panel of 6 people of median sensitivity to l-menthol.

Panel Selection

To select a test panel of average sensitivity the following procedure is used. Known quantities of l-menthol in solution in petroleum ether (bp. 40-60) are placed on 5 mm squares of filter paper, whereafter the solvent is allowed to evaporate. A panel of observers is enrolled and asked to place one impregnated square at a time on the tongue and to report on the presence or absence of a cooling effect. The quantity of l-menthol on each impregnated square is gradually reduced from a value substantially above 0.25 $\mu$g. per square to substantially below 0.25 $\mu$g, the precise range being immaterial. Conveniently, one starts with squares containing 2.0 $\mu$g l-menthol, the amount on each successive square being half that of the preceding square, i.e. the second test square will contain 1.0 $\mu$g, the third 0.5 $\mu$g and so on. Each quantity is tested on the tongue at least 10 times. In this way, the thresholds to cold receptor stimulus by l-menthol are determined for each individual of the panel, the threshold for each individual being that amount of l-menthol for which, in a series of not less than 10 test applications, a cooling effect is reported 50% of the time. Six panel members are now selected whose threshold to l-menthol is in the range 0.1 $\mu$g to 10 $\mu$g and whose average threshold is approximately 0.25 $\mu$g, this select panel being regarded as the test panel of average sensitivity.

Compound Testing

To test the activity of compounds according to this invention, the above procedure is repeated using only the 6 selected panel members of average sensitivity to l-menthol. The individual thresholds for each test compounds on each of the 6 selected panel members are determined and averaged. Those compounds whose average threshold on the select test panel is 100 $\mu$g or less or regarded as having cooling activity in accordance with this invention.

Test Results

The following tables set out the relative cooling activities of compounds of the formula defined above when tested according to the foregoing procedure.

TABLE I

Acids

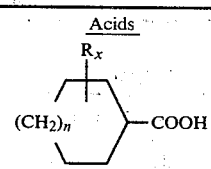

| Compound | b.p. | Activity ($\mu$g) |
|---|---|---|
| 1-sec. butylcycloheptanecarboxylic acid | 144°/3mm | 2 |
| 1-isopropyl butylcycloheptanecarboxylic acid | 119-20°/1mm | 2 |
| 2-isopropyl butylcycloheptanecarboxylic acid | 115°/0.2mm | 3 |
| 1-isopropyl-2-methyl butylcycloheptanecarboxylic acid | 112-6°/0.03mm | 4 |
| 1-ethyl-2-methyl butylcycloheptanecarboxylic acid | 112°/0.05mm | 15 |
| 1-ethyl butylcycloheptanecarboxylic acid | 111-5°/1mm | 35 |
| 2-ethyl butylcycloheptanecarboxylic | | |

TABLE I-continued

Acids

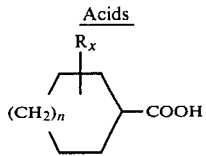

| Compound | b.p. | Activity (μg) |
|---|---|---|
| acid | 100–2°/0.25mm | 17 |
| 1,4,4-trimethyl butylcycloheptane-carboxylic acid | 99°/0.2mm | 5 |
| 1-ethylcyclooctanecarboxylic acid | 136–138°/0.2mm | 20 |
| 2-ethylcyclooctanecarboxylic acid | 117–21°/0.025mm | 12 |
| 1-isopropyl-2-methylcyclopentane-carboxylic acid | 94–5°/0.4mm | 15 |
| 1-isopropyl-2-methylcyclopentane-carboxylic acid | 91–4°/0.5mm | 20 |
| 1-isopentyl-2-methylcyclopentane-carboxylic acid | 106–8°/0.4mm | 8 |
| 1-sec. butyl-2-methylcyclopentane-carboxylic acid | 88–91°/0.02mm | 4 |

TABLE II

Esters

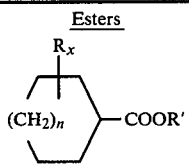

| Compound | b.p. | Activity (μg) |
|---|---|---|
| 2'-hydroxyethyl 1-isopropyl-2-methyl-cyclopentanecarboxylate | 102°/0.01mm | 3 |
| 2'-hydroxy-n-propyl 1-isopentylcyclo-pentanecarboxylate | 108–10°/0.3mm | 12 |
| 2'-hydroxyethyl 1-isopropylcyclo-heptanecarboxylate | 104°/0.7mm | 2 |
| 2'-hydroxyethyl 1-sec. butylcyclo-heptanecarboxylate | 95°/0.01mm | 1.5 |
| 2'-hydroxyethyl 1-ethyl-2-methylcyclo-heptanecarboxylate | 130°/0.3mm | 3 |
| 2'-hydroxyethyl 1-isopropyl-2-methyl cycloheptanecarboxylate | 115–7°/0.25mm | 3 |
| 2'-hydroxyethyl 1-ethylcycloheptane-carboxylate | 109°/0.7mm | 6 |
| 2'-hydroxyethyl 1-ethylcyclooctane-carboxylate | 105–6°/0.05mm | 10 |
| 2'-hydroxyethyl 2-ethylcyclooctane-carboxylate | 108°/0.01mm | 2 |
| 1'-methyl-2'-hydroxy-n-propyl 1-isopropyl-cycloheptanecarboxylate | 99°/0.01mm | 6 |

TABLE III

Carboxamides

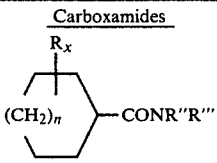

| Compound | mp/bp | Activity (μg) |
|---|---|---|
| N,1-diisopropyl-2-methylcyclo-pentanecarboxamide | 90.5–91.5°(mp) | 0.5 |
| N-ethyl-1-isopropyl-2-methylcyclo-pentanecarboxamide | 85°/0.02mm(bp) | 0.7 |
| N-(1-isopropyl-2-methylcyclopentane-carbonyl)-glycine ethyl ester | 65–7°(mp) | 2 |
| N-(5'-hydroxy-n-pentyl)-1-isopropyl-2-methylcyclopentanecarboxamide | 162°/0.01mm(bp) | 3 |

TABLE III-continued

Carboxamides

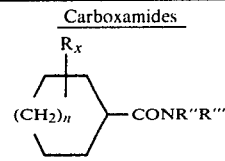

| Compound | mp/bp | Activity (μg) |
|---|---|---|
| N,1-diisopropylcyclopentane-carboxamide | 110–2°(mp) | 2 |
| N-(1-isopropylcyclopentane-carbonyl)-glycine ethyl ester | 85–6°(mp) | 0.7 |
| N-(1-isopropylcyclopentanecarbonyl)-piperidine | 98–101°/0.2mm(bp) | 2 |
| 1-isopropylcyclopentanecarboxamide | 67–8°(mp) | 10 |
| N-p-hydroxyphenyl-1-isopropylcyclo-pentanecarboxamide | 141–4°(mp) | 10 |
| N-ethyl-1-isopentylcyclopentane-carboxamide | 106–9°/0.1mm(bp) | 1.5 |
| N-2'-hydroxyethyl-1-isopentylcyclo-pentanecarboxamide | 143–6°0.1mm(bp) | 4 |
| N-ethyl-1-sec. butylcyclopentane-carboxamide | 98–100°(mp) | 1.5 |
| N-(1',1'-dimethyl-2-'-hydroxyethyl)-1-isopropylcycloheptanecarboxamide | 121°/0.02mm(bp) | 2 |
| N,2-dimethyl-1-ethylcycloheptane-carboxamide | 113°/0.4mm(bp) | 1.5 |
| N,1-diethyl-2-methylcycloheptane-carboxamide | 125–7°/0.4mm(bp) | 1 |
| N-(1-ethyl-2-methylcycloheptane-carbonyl)-glycine ethyl ester | 65–7°(mp) | 2 |
| N-(2'-hydroxyethyl)-N,2-dimethyl-1-ethylcycloheptanecarboxamide | 152–5°/0.3mm(bp) | 5 |
| N-(1-ethyl-2-methylcycloheptane-carbonyl)-pyrrolidine | 131°/0.3mm(mp) | 2 |
| N-(1-ethyl-2-methylcycloheptane-carbonyl)-morpholine | 145–7°/0.3mm(bp) | 2 |
| N-(1-ethyl-2-methylcycloheptanecar-bonyl)-N-methyl-glycine ethyl ester | 130–2°/0.3mm(bp) | 5 |
| N-(1-ethyl-2-methylcycloheptane-carbonyl)-glycine methyl ester | 150–2°/0.4mm(bp) | 3 |
| N-p-methoxyphenyl-1-ethyl-2-methyl-cycloheptanecarboxamide | 107–8°(mp) | 6 |
| N-methyl-2-ethylcycloheptane-carboxamide | 56–8°(mp) | 4 |
| N-(2-ethylcycloheptanecarbonyl)-glycine ethyl ester | 45–6°(mp) | 5 |
| N,1,4,4-tetramethylcycloheptane-carboxamide | 75°/0.005mm(bp) | 2 |
| N-ethyl-1,4,4-trimethylcycloheptane-carboxamide | 85°/0.005mm(bp) | 2 |
| N-ethyl-1-isopropylcycloheptane-carboxamide | 74.5–75.5°(mp) | 0.7 |
| N-(1-isopropylcycloheptanecarbonyl)-glycine ethyl ester | 88.5°(mp) | 0.7 |
| N-ethyl-1-sec.butylcycloheptane-carboxamide | 76–77°(mp) | 0.7 |
| N-(1-sec.butylcycloheptanecarbonyl)-glycine ethyl ester | 96.5–97.5(mp) | 0.5 |
| N-(1',1'-dimethyl-2'-hydroxyethyl)-1-sec. butylcycloheptanecarboxamide | 95°/0.01mm(bp) | 0.7 |
| N-ethyl-2-isopropylcycloheptane-carboxamide | 75–77°(mp) | 0.7 |
| N-t-butyl-2-isopropylcycloheptane-carboxamide | 107–8°(mp) | 0.3 |
| N-(2-isopropylcycoheptanecarbonyl)-glycine ethyl ester | 155°/0.01mm(bp) | 0.7 |
| N-ethyl-1-isopropyl-2-methylcyclo-heptanecarboxamide | 115–20°/0.3mm(bp) | 0.3 |
| N-methyl-1-isopropyl-2-methylcyclo-heptanecarboxamide | 113–115°(mp) | 0.1 |
| N-(1-isopropyl-2-methylcycloheptane-carbonyl)-glycine ethyl ester | 135–140°/0.3mm(bp) | 0.4 |
| N-(2'-hydroxyethyl)-N-methyl-1-isopropyl-2-methylcycloheptane-carboxamide | 150–4°/0.3mm(bp) | 0.5 |
| N,1-diethylcycloheptanecarboxamide | 99°/0.03mm(bp) | 1 |
| N-(1-ethylcyclopheptanecarbonyl)-glycine ethyl ester | 68–9°(mp) | 2 |

TABLE III-continued

Carboxamides $$(CH_2)_n \begin{array}{c} R_x \\ \diagdown \end{array} CONR''R'''$$

| Compound | mp/bp | Activity (μg) |
|---|---|---|
| N-(1',1'-dimethyl-2'-hydroxyethyl)-1-ethylcycloheptanecarboxamide | 140°/0.7mm(bp) | 1.5 |
| N-(3,3,7-trimethylcycloheptane-carbonyl)-glycine ethyl ester | 77–8°(mp) | 2 |
| N-ethyl-3,3,7-trimethylcycloheptanecarboxamide | 82–3°(mp) | 5 |
| N,3,3,7-tetramethylcycloheptanecarboxamide | 108–10°(mp) | 5 |
| N-(1',1'-dimethyl-2'-hydroxyethyl)-3,3,7-trimethylcyclopheptanecarboxamide | 135°/0.015mm(bp) | 6 |
| N,N-dimethyl-1-ethylcyclooctanecarboxamide | 113°/0.8mm(bp) | 1.5 |
| N-(1-ethylcyclooctanecarbonyl)-glycine ethyl ester | 65–7°(mp) | 1.5 |
| N-(1',1'-dimethyl-2'-hydroxyethyl)-1-ethylcyclooctanecarboxamide | 142–5°/0.7mm(bp) | 15 |
| N,2-diethylcyclooctanecarboxamide | 117°/0.01mm(bp) | 0.7 |
| N-(2-ethylcyclooctanecarbonyl)-glycine ethyl ester | 147°/0.01mm(bp) | 1.5 |
| N-(1',1'-dimethyl-2'-hydroxyethyl)-2-ethylcyclooctanecarboxamide | 65–6°(mp) | 3 |
| N-methyl-2-ethylcyclooctanecarboxamide | 115°/0.005mm(bp) | 1 |
| N-methyl-1-ethylcycloundecanecarboxamide | 150°/0.005mm(bp) | 20 |
| N,1-diethylcycloundecanecarboxamide | 91–2°(mp) | 20 |
| N-(1',1'-dimethyl-2'-hydroxyethyl)-1-ethylcycloundecanecarboxamide | 99–101°(mp) | 20 |
| N-(1-ethylcycloundecanecarbonyl)-glycine ethyl ester | 65–67°(mp) | 20 |
| N,N-dimethyl-1-ethylcycloundecanecarboxamide | 116°/0.005mm(bp) | 17 |
| N-(3',4'-dimethoxyphenyl)-1-isopropylcycloheptanecarboxamide | 99–100°(mp) | 5 |
| N-(3'-hydroxy-4'-methylphenyl)-1-isopropylcycloheptanecarboxamide | 96–98°(mp) | 1 |
| N-(3',4'-dimethylphenyl)-2-isopropylcycloheptanecarboxamide | 125–126°(mp) | 15 |
| N-(2'-methyl-4'-methoxyphenyl)-1-isopropylcycloheptanecarboxamide | 98–99°(mp) | 0.2 |
| N-(cyclopentyl)-1-isopropylcycloheptanecarboxamide | 93–95°(mp) | 0.5 |
| N-n-octyl-1-isopropylcycloheptanecarboxamide | 115°/0.3mm(bp) | 8 |

As indicated by the activities listed above, the compounds of high activity are those having an isopropyl or sec. butyl substituent in the 1- or 2-position in the ring, with the amides generally being more active than the acids and esters. To compounds of highest activity, and therefore the preferred compounds for most uses (although in some cases it may be preferred to use compounds of lower activity for other reasons, for example, a particular odour, or enhanced skin penetration) are the amides having an isopropyl or sec. butyl group in the 1- or 2-position.

The cold receptor stimulants used in this invention find utility in a wide variety of consumer products for consumption by or application to the human body. Broadly speaking, these products can be divided into ingestibles and topicals, both terms being taken in their broadest possible sense. Thus ingestible is to be taken as including not only foodstuffs and beverages taken into the mouth and swallowed, but also other orally ingested products taken for reasons other than their nutritional value, e.g. indigestion tablets, antacid preparations, laxatives, etc. Ingestible is also to be taken to include edible compositions taken by mouth, but not necessarily swallowed, e.g. chewing gum. Topical is to be taken as including not only compositions such as perfumes, powders and other toiletries, lotions, liniments, oils and ointments, applied to the external surfaces of the human body, whether for medical or other reasons, but also compositions applied to, or which, in normal usage, come in contact with, internal mucous membranes of the body, such as those of the nose, mouth or throat, whether by direct or indirect application, mouthwash and gargle compositions. Topical products, in this context, also include toilet articles such as cleansing tissues and toothpicks.

In formulating the products of this invention the cold receptor stimulants will be incorporated into a vehicle by means of which the compound may be applied to the person. The vehicle may, itself be completely inert or it may, and usually will, contain other active ingredients. A wide variety of vehicles will be suitable, depending upon the particular product involved, such vehicles including solids, liquids, emulsions, foams and gels. Typical vehicles for the cold receptor stimulants include aqueous or alcoholic solutions, oils and fats such as hydrocarbon oils, fatty acid esters, long chain alcohols and silicone oils; finely divided solids such as starch or talc; cellulosic materials such as paper tissue; low-boiling hydrocarbons and halohydrocarbons used as aerosol propellants; gums and natural or synthetic resins.

Generally, these vehicles will contain at least one or more of the following adjuvants: flavourants, colourants, perfuming agents, surface active agents, antiseptic agents, such as are usually employed in topical and ingestible compositions.

A more detailed discussion of particular products according to this invention follows:

Toiletries and Cosmetics

A major area of utility of the cold receptor stimulants of this invention will be in the field of toilet preparations broadly classed as personal care products. These may be defined as manufactured products applied to the person for the purposes of grooming or hygiene or for cosmetic purposes, including make up and perfumery, but excluding ethical and proprietary medical preparations. Particular personal care products are discussed hereinafter by way of example and are illustrated hereinafter in the specific examples.

One class of personal care product into which the compounds of this invention may be incorporated is represented by lotions for topical application, e.g. aftershave lotions, toilet water etc. where the compound will be used in alcoholic or aqueous alcoholic solutions, such solutions usually also containing a perfume or mild antiseptic or both. The amount of compound added to the formulation will usually be in the range of 0.1 to 5% by weight based on the total composition.

Another class of personal care product is represented by soap and soap-based compositions where the compounds will be used in combination with an oil or fat or a natural or synthetic surfactant e.g. a fatty acid salt or a laurylsulphate salt, the composition usually also containing an essential oil or perfume. The range of soap compositions will include soaps of all kinds e.g. toilet soaps, shaving soaps, shaving foams etc. particularly shaving foams of the aerosol type. Usually the compound will be added to the formulation in amount of from 0.5 to 5% by weight.

A further class of personal care products into which the cold receptor stimulants may be incorporated is represented by cosmetic creams, emollients and lotions, such creams, emollients and lotions usually comprising an oil-in-water emulsion as a base and optionally containing a range of other ingredients such as wax, preservative, perfume, antiseptics, astringents, pigments etc. Also included within this class are lipstick compositions, such compositions usually comprising an oil and wax base into which the coolant can be incorporated along with other ingredients e.g. pigments. Once again the formulation of such products, apart from the incorporation of the cold receptor stimulant, usually in an amount of from 0.01 to 5% by weight, as conventional.

Personal care products for oral hygiene into which the cold receptor stimulants of this invention can be incorporated include mouthwash, gargle and dentifrice compositions. The first two may be considered together and will usually comprise an aqueous, alcoholic or aqueous-alcoholic solution of an antiseptic often coloured or flavoured for palatability, to which the cold receptor stimulant is added in an amount of from 0.01 to 1% by weight.

Dentifrice compositions may be of the solid block, powder, paste or liquid type and will usually comprise a finely divided abrasive or polishing material, e.g. precipitated chalk, silica, magnesium silicate, aluminium hydroxide or other similar materials well known in the art, and a detergent or foaming agent. Optional ingredients which may also be included are flavouring agents and colourants, antiseptics, lubricants, thickeners, emulsifiers or plasticisers. The amount of cold receptor stimulant added in such compositions will generally be from 0.1 to 1.0% by weight based on the total composition.

Edible and Potable Compositions

The cold receptor stimulants of this invention may be incorporated into a wide range of edible and potable compositions comprising an edible or potable base and usually one or more flavouring or colouring agents. The particular effect of the cold receptor stimulant is to create a cool or fresh sensation in the mouth, and in some cases, even in the stomach, and therefore the compounds find particular utility in sugar-based confectionery such as chocolate, boiled sweets, mints and candy, in ice cream and jellies and in chewing gum. The formulation of such confections will be by traditional techniques and according to conventional recipes and as such forms no part of this invention. The cold receptor stimulant will be added to the recipe at a convenient point and in amount sufficient to produce the desired cooling effect in the final product. As already indicated, the amount will vary depending upon the particular compound, the degree of cooling effect desired and the strength of other flavourants in the recipe. For general guidance, however, amounts in the range 0.01 to 5.0% by weight based on the total composition will be found suitable.

Similar considerations apply to the formulation of beverages. Generally speaking the compounds will find most utility in soft drinks, e.g. fruit squashes, lemonade, cola etc., but may also be used in alcoholic beverages. The amount of compound used will generally be in the range 0.001 to 2.5% by weight based on the total composition.

Medicaments

Because of their cooling effect on the skin and on the mucous membrane of the mouth, throat and nose and of the gastrointestinal tract the cold receptor stimulants may be used in a variety of oral medicines, nasal and throat sprays, and topical compositions, particularly where a counterirritant is required. Generally speaking, these medical preparations, whether topical or ingestible, proprietary or ethical, will contain a pharmaceutically acceptable carrier, either liquid or solid, a pharmaceutically active ingredient and into these preparations the cold receptor stimulants of this invention can readily be incorporated to provide a pleasant cooling effect on the skin, or other surface tissues of the body, or in the mouth or gastrointestinal tract depending on particular preparation and whether it is to be applied externally or internally. A particular utility for the compounds of this invention is in the formulation of antacid and indigestion remedies, and especially those based on sodium or magnesium hydroxide or magnesium trisilicate. In such compositions the compound will usually be added in an amount of from 0.01 to 1.0% by weight.

The cold receptor stimulants may also be included in oral analgesic compositions e.g. with acetyl salicylic acid or its salts, and in nasal decongestants e.g. those containing ephedrine.

Consumer products according to the invention are illustrated by the following Examples in which all percentages are by weight.

EXAMPLE 1

After Shave Lotion

An after shave lotion was prepared according to the following recipe by dissolution of the ingredients in the liquid and cooling and filtering:

| Denatured Ethanol | 75% |
|---|---|
| Diethylphthalate | 1.0% |
| Propylene Glycol | 1.0% |
| Lactic Acid | 1.0% |
| Perfume | 3.0% |
| Water | to 100% |

Into the base lotion was added 1.0% by weight of N-(1-ethylcyclooctanecarbonyl)glycine ethyl ester.

When the final solution was applied to the face a clearly noticeable cooling effect became apparent after a short interval of time.

EXAMPLE 2

Antiseptic Ointment

An ointment was prepared according to the following formulation:

| Cetyltrimethyl ammonium bromide | 4.0% |
|---|---|
| Cetyl Alcohol | 6.0% |
| Stearyl Alcohol | 6.0% |
| White Paraffin | 14.0% |
| Mineral Oil | 21.0% |
| Water | to 100% |

The ingredients were mixed, warmed to 40° C. and emulsified in a high speed blender. Added to the mixture during blending was 1.0% of 2'-hydroxyethyl 1-isopropylcycloheptane carboxylate.

The final ointment when applied to the skin gave rise to a cooling effect.

EXAMPLE 3

Cleansing Tissue

A cleansing liquid was prepared having the formulation:

| | |
|---|---|
| Triethanolamine Lauryl sulphate | 1.0% |
| Glycerol | 2.0% |
| Perfume | .95% |
| Water | to 100% |

To this liquid was added 2.0% of 1-isopropylcycloheptanecarboxylic acid. A paper tissue was then soaked in the liquid.

When the impregnated tissue was used to wipe the skin a fresh cool sensation developed on the skin after a short interval.

EXAMPLE 4

Toothpaste

The following ingredients were mixed in a blender:

| | |
|---|---|
| Dicalcium phosphate | 48.0% |
| Sodium lauryl sulphate | 2.5% |
| Glycerol | 24.8% |
| Sodium carboxymethyl cellulose | 2.0% |
| Citrus flavourant | 1.0% |
| Sodium saccharin | 0.5% |
| Water | to 100% |

Shortly before completion of the blending operation 0.5% by weight of N-ethyl-1-isopropylcycloheptanecarboxamide was added to the blender.

When applied as a toothpaste a pleasant cooling effect is noticed in the mouth.

EXAMPLE 5

Aerosol Shaving Soap

An aerosol shaving soap composition was formulated according to the following recipe:

| | |
|---|---|
| Stearic Acid | 6.3% |
| Lauric Acid | 2.7% |
| Triethanolamine | 4.6% |
| Sodium Carboxymethyl Cellulose | 0.1% |
| Sorbitol | 5.0% |
| Water | to 100% |
| Perfume | 0.5% |

The composition was prepared by fusing the acids in water, adding the triethanolamine, cooling and adding the other constituents. To the mixture was then added 0.5% of N-(1',1'-dimethyl-2'-hydroxyethyl)-1-ethylcycloheptanecarboxamide. The composition was then packaged in an aerosol dispenser under pressure of a butane propellant.

When used in shaving a fresh cool sensation was noticed on the face.

EXAMPLE 6

Soft Drink

A soft drink concentrate was prepared from the following recipe:

| | |
|---|---|
| Pure orange juice | 60% |
| Sucrose | 10% |
| Saccharin | 0.2% |
| Orange flavouring | 0.1% |
| Citric acid | 0.2% |
| Sulphur dioxide | trace amount |
| Water | to 100% |

To the concentrate was added 0.05% of 2'-hydroxyethyl 1-ethylcyclooctanecarboxylate.

The concentrate was diluted with water and tasted. An orange flavour having a pleasantly cool after-effect was obtained.

EXAMPLE 7

Toothpick

The tip of a wooden toothpick was impregnated with an alcoholic solution containing N,N-dimethyl-1-ethyl-cyclooctanecarboxamide in an amount sufficient to deposit on the toothpick 0.05 mg. of the compound. The toothpick was then dried.

When placed against the tongue a cool sensation is noticed after a short period of time.

EXAMPLE 8

Eye Lotion

An eye lotion was prepared containing the following ingredients:

| | |
|---|---|
| Witch Hazel | 12.95% |
| Boric Acid | 2.00% |
| Sodium Borate | 0.50% |
| Allantoin | 0.05% |
| Salicylic Acid | 0.25% |
| Chlorobutol | 0.02% |
| Zinc Sulphate | 0.004% |
| Water | to 100% |

To the formulation was added 0.003% based on the total composition, of N,1-diethylcycloundecanecarboxamide. When used to bathe the eyes a cool fresh sensation is apparent on the eyeball and eyelids.

EXAMPLE 9

Toilet Water

A toilet water was prepared according to the following recipe:

| | |
|---|---|
| Denatured ethanol | 75.0% |
| Perfume | 5.0% |
| Water | to 100% |

To the recipe was added 0.5% based on the total composition, of N-methyl-1-isopropyl-2-methylcycloheptanecarboxamide.

As with the after shave lotion, a cooling effect was clearly noticeable on the skin well after the termination of any cooling effect attributable to the evaporation of the alcoholic carrier.

EXAMPLE 10

Soft Sweet

Water was added to icing sugar at 40° C. to form a stiff paste. 0.05% of N-2'-hydroxyethyl-N-methyl-1-isopropyl-2-methylcycloheptanecarboxamide was then stirred into the paste and the mixture allowed to set. A soft sweet mass resulted having the characteristic cooling effect in the mouth of peppermint but without the minty flavour or odour.

EXAMPLE 11

Indigestion Tablet

The following ingredients were ground together:

| | |
|---|---|
| Magnesium carbonate | 49.5% |
| Sorbitol | 49.4% |
| Saccharin | 0.1% |
| Talc | 1.0% |

Added to the mixture during grinding was 0.05% of N,1-diethyl-2-methylcycloheptanecarboxamide. After mixing the mixture was pressed into 0.5 g tablets. Taken by mouth and swallowed the tablets produced, after a short interval of time, a noticeable cooling effect in the stomach.

EXAMPLE 12

Hydrophilic Ointment

A hydrophilic ointment was prepared having the following formulation:

| | |
|---|---|
| Propylene Glycol | 12% |
| 1-Octadecanol | 25% |
| White Soft Paraffin | 25% |
| Sodium lauryl sulphate | 1% |
| Water | to 100% |

The sodium lauryl sulphate was added to the water and heated to 60° C. The paraffin was melted by heating to 60° C. and was then added to the sodium lauryl sulphate mixture with stirring. Propylene glycol and 1-octadecanol were then added to this mixture.

To the resultant mixture was added 2% of N-(1-isopropylcyclopentanecarbonyl) peridine. The final ointment when applied to the skin gave rise to a marked cooling effect.

EXAMPLE 13

Deodorant Composition

A deodorant composition suitable for formulation and dispensing as an aerosol under pressure of a suitable propellant was formulated according to the following recipe:

| | |
|---|---|
| Denatured ethanol | 96.9% |
| Hexachlorophene | 2.0% |
| Isopropyl myristate | 1.0% |
| Perfume | 0.1% |

To the composition was added 13% by weight of N-ethyl-1-isopropyl-2-methylcyclopentanecarboxamide.

Application of the final composition gave rise to a definite cooling sensation on the skin.

EXAMPLE 14

Lipstick 0.06% by weight of N-t-butyl-2-isopropylcycloheptanecarboxamide was incorporated into a proprietary lipstick by melting the lipstick, adding the compound, and allowing the lipstick to resolidify. When applied to the lips a persistant cooling effect is clearly noticeable.

EXAMPLE 15

Solid Cologne

A solid cologne was formulated according to the following recipe:

| | |
|---|---|
| Denatured ethanol | 74.5% |
| Propylene glycol | 3.0% |
| Sodium stearate | 5.0% |
| Perfume | 5.0% |
| Water | to 100% |

The sodium stearate was dissolved by stirring in a warm mixture of the ethanol, propylene glycol and water. To the solution was added the perfume and 3.0% of N-methyl-2-ethylcycloheptanecarboxamide and the mixture then allowed to solidify into a waxy cake.

When applied to the forehead a strong cooling effect is obtained.

EXAMPLE 16

Hair Tonic

A hair tonic was formulated containing:

| | |
|---|---|
| Denatured ethanol | 84.5% |
| Castor Oil | 14.0% |
| Resorcinol | 0.5% |
| Perfume | 1.0% |

The castor oil, resorcinol and perfumes were dissolved in the ethanol component and to the solution was added 2% of N-2'-hydroxyethyl-N-methyl-1-isopropyl-2-methylcycloheptanecarboxamide. When rubbed on the scalp a cooling effect is noticed.

EXAMPLE 17

Mouthwash

A concentrated mouthwash composition was prepared according to the following recipe:

| | |
|---|---|
| Ethanol | 3.0% |
| Borax | 2.0% |
| Sodium bicarbonate | 1.0% |
| Glycerol | 10.0% |
| Flavourant | 0.4% |
| Thymol | 0.03% |
| Water | to 100% |

To the composition was added 0.1% of N,1-diisopropyl-2-methylcyclopentanecarboxamide.

When diluted with approximately 10 times its own volume of water and used to rinse the mouth a strong cooling effect is obtained in the mouth.

EXAMPLE 18

Talcum Powder

A talcum powder was prepared by grinding together the following:

| | |
|---|---|
| Low micron talc | 90% |
| Zinc stearate | 5% |
| Starch | 5% |

In the course of grinding there was added 3% of N-ethyl-1-sec. butylcycloheptanecarboxamide. A talcum powder having a freshening and cooling effect was obtained.

EXAMPLE 19

Chewing Gum

Leaves of a proprietary chewing gum were leached in running water for 168 hours to remove all water-soluble flavourants. At the end of the leaching operation the chewing gum base had no detectable minty odour or flavour. The chewing gum base was then kneaded with 4% of 2'-hydroxyethyl-1-sec.butylcycloheptanecarboxylate. When compared with the water-extracted chewing gum base, the final product showed no distinguishable change in flavour but showed a marked cooling effect in the mouth.

The above Examples illustrate the range of compounds and the range of compositions included within the present invention. However, they are not to be taken as limitir; the scope of the invention in any way. Numerous other compounds within the general formula will be equally suitable for use in the compositions of Examples 1–19 and the physiological cooling effect obtained with the compounds of the invention will recommend their use in a wide variety of other compositions where the cooling effect will be of value.

The carboxylic acids, esters and amides hereinbefore referred to as cold receptor stimulants in ingestible and topical compositions also find utility as cold receptor stimulants in tobacco and tobacco-containing manufactures.

As has already been mentioned, menthol is extensively used for this purpose notwithstanding its strong minty odour and relative volatility. Other similar compounds have also been proposed as alternatives to menthol in tobacco, see for example, the various publications hereinbefore referred to. Still other compounds have been proposed as 'flavourants' in tobacco rather than 'coolants' and amongst these may be mentioned 2-isopropyl-5-methyl methyl hexanol alternatively named 2,6-dimethylhept-3-yl methanol) and related compounds as disclosed in U.S. Pat. No. 3,704,714. Notwithstanding these various disclosures a need still exists for alternatives to menthol for incorporating into tobacco to provide a 'cool' effect when smoked.

It is a further object of the present invention, therefore, to provide tobacco and tobacco-containing manufactures containing an ingredient which creates a 'cool' sensation when the ingredient comes into contact with the nasal and oral mucosa, either in the tobacco smoke, or by direct contact of the tobacco on the nasal or oral mucosa, but which are not subject to the disadvantages of a strong minty flavour and storage instability.

It is a yet further object of the present invention to provide an improved method of imparting to tobacco and tobacco-containing manufactures a physiological cooling activity.

According to the present invention, therefore, there are also provided tobacco and tobacco-containing manufactures comprising tobacco and a cold receptor stimulating additive, present in an amount effective to stimulate the cold receptors of the nervous system of mucous membranes of the oral and nasal mucosa when the tobacco or tobacco-containing manufacture is smoked, chewed or inhaled by the human user, said additive being a cold receptor stimulating substituted carboxylic acid, ester or amide of the formula hereinbefore defined.

By tobacco and tobacco-containing manufactures we mean any article, such as a cigarette or cigar, or any composition, such as pipe or chewing tobacco or snuff, containing tobacco in a prepared form for utilisation by the human person whether by smoking, i.e. burning of the prepared tobacco and inhalation of the tobacco smoke, chewing or direct inhalation of the tobacco.

In formulating the tobacco and tobacco-containing manufactures of this invention the active compound may be incorporated directly into the tobacco, for example, by impregnation of the tobacco with an alcoholic solution of the active ingredient, at a suitable stage of manufacture.

However, in an alternative and preferred arrangement, the active ingredient may be incorporated into a tobacco smoke filter for use in a pipe or cigarette filter or as a filter tip for cigarette. The latter, in particular, forms a particularly effective utilisation of the present invention, the active compound simply being impregnated in the wad of material forming the filter tip. This may be of any of the well known types of filter tip for cigarettes, e.g. a filter pad of cellulose acetate, paper, cotton, α-cellulose or asbestos fibre. Conveniently the filter tip is impregnated with an alcoholic solution of the active compound and then dried to deposit the active compound therein.

The amount of active compound to be incorporated into the tobacco or tobacco-containing manufacture in accordance with the invention will vary from compound to compound depending on the activity thereof, i.e. the amount thereof which it is necessary to place in contact with the skin to produce a noticeable cooling effect, and will depend also on the mode of application thereof, i.e. whether the compound is impregnated in the tobacco itself, or in a filter tip or in any other accessary. However, the actual amount is not critical to this invention and will be readily determinable by the person skilled in the art by means of a few simple tests. As a matter of guidance, however, it may be mentioned that with the more active compounds, as little as 0.01 mg deposited on the filter tip of a tipped cigarette is effective.

This latter aspect of the invention is illustrated by the following Examples.

EXAMPLE 20

Cigarette Tobacco

A proprietary brand of cigarette tobacco was sprayed with an ethanolic solution of N,1-diisopropyl-2-methylcyclopentanecarboxamide and was rolled into cigarettes each containing approximately 0.1 mg. of active compound. Smoking the impregnated cigarettes produced a cool effect in the mouth characteristics of metholated cigarettes but without any attendant odour other than that normally associated with tobacco.

EXAMPLE 21

Filter Tip Cigarettes

The filter tip of a proprietary brand of cigarette was impregnated with an ethanolic solution of N-ethyl 1-sec. butylcycloheptanecarboxamide in amount sufficient to deposit in the filter 0.1 mg of the active compound. Smoking the cigarette with the impregnated tip gave rise to a noticeable cooling effect in the mouth.

EXAMPLE 22

Pipe Tobacco

A proprietary brand of pipe tobacco was sprayed with an ethanolic solution of N-t-butyl-2-isopropylcycloheptanecarboxamide 2 g of the tobacco containing 5 mg of the active compound was placed in a pipe. Smoking the impregnated tobacco produced a cool effect in the mouth characteristics of mentholated tobacco but without any attendant odour other than that normally associated with tobacco.

EXAMPLE 23

Cigars

The tobacco of a proprietary brand of cigar was impregnated with an ethanolic solution of N-ethyl-1-isopropylcycloheptanecarboxamide in an amount sufficient to deposit in the cigar 5 mg of the active compound. Smoking the cigar with the impregnated tobacco gave rise to a noticeable cooling effect in the mouth.

EXAMPLE 24

Chewing Tobacco

A proprietary brand of chewing tobacco was impregnated with an ethanolic solution of 2'-hydroxyethyl 2-ethylcyclooctanecarboxylate. 1 g of the tobacco containing 0.5 mg of active compound was used. Chewing the impregnated tobacco produced a cool effect in the mouth.

EXAMPLE 25

Snuff

A proprietary brand of snuff was impregnated with an ethanolic solution of N,1-diethylcycloheptanecarboxamide. 1 g of the snuff was impregnated with 5 mg of active compound. About 0.01 g of the impregnated snuff produced a cool effect in the nose when inhaled.

In yet another aspect of this invention, there are provided a group of novel compounds having utility as cold receptor stimulants in a variety of ingestible and topical compositions, and in tobacco and tobacco-containing preparations, as hereinbefore described. These novel compounds are alicyclic carboxamides of the formula III:

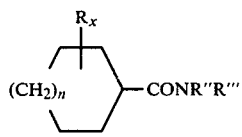

III where n is 0 or an integer of from 2-6 inclusive:

x has a value of 1, 2 or 3:

R is $C_1$-$C_5$ alkyl, at least one R group being in a 1,2 or 3-position relative to the carboxamide group and the total number of carbon atoms provided by the R groups and the carbocycle to which they are attached being from 8-14, preferably 8-12:

R'', when taken separately, is H or $C_1$-$C_5$ alkyl;

R''', when taken separately, is $C_1$-$C_{10}$ alkyl or hydroxyalkyl, or alkylcarboxyalkyl of up to 8 carbon atoms, with the proviso that when R'' is H, R''' may also be cycloalkyl of up to 8 carbon atoms, phenyl or substituted phenyl containing alkyl, hydroxy or methoxy substituents and a total of up to 10 carbon atoms; and R'' and R''', when taken together, represent an alkylene group of up to 8 carbon atoms, the carbon atom chain of which may optionally be interrupted by an oxygen atom;

with the provisos that:

(i) where n is 0 and x is 2, with one R group being isopropyl in the 1-position and the other R group being in the 2-position, then said other R group contains at least 2 carbon atoms, when R'' is H and R''' is phenyl: and (ii) where n is 0 and x is 2, with one R group being isopropyl in the 3-position and the other R group being in the 1-position, then said other R group contains at least 2 carbon atoms, when R'' and R''' are both ethyl.

Compounds of especial interest are of the formula:

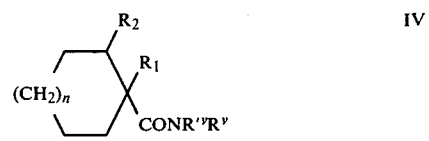

IV where n is 2 or 3:

one of $R_1$ and $R_2$ is $C_1$-$C_5$ alkyl and the other is H or $C_1$-$C_5$ alkyl:

R$'^v$, when taken separately, is H or $C_1$-$C_5$ alkyl:

R$^v$, when taken separately, is $C_1$-$C_5$ alkyl or hydroxyalkyl, or alkylcarboxyalkyl of up to 6 carbon atoms, or, when R$'^v$ is H, $C_5$-$C_6$ cycloalkyl, phenyl or phenyl containing hydroxy, methyl or methoxy substituents: and R$'^v$ and R$^v$, when taken together, represent an alkylene group of up to 8 carbon atoms, the carbon atom chain of which may optionally be interrupted by oxygen.

Of especial interest are cycloheptane- and cyclooctane-carboxamides of formula IV where one of $R_1$ and $R_2$ is a $C_3$-$C_5$ alkyl group having branching in an alpha position relative to the ring, and especially an isopropyl or sec. butyl group.

The novel amides of this invention may be prepared by the methods hereinbefore described and as illustrated in the following Examples:

EXAMPLE 26

Preparation of N-ethyl-2-isopropylcycloheptanecarboxamide

Part A

A Schiff's base was prepared from cycloheptanone (56 g. 0.5 mole) and aniline (46.5 g, 0.5 mole) in dry toluene containing a catalytic amount of p-toluene sulphonic acid.

A quantity of the above Schiff's base (66.5 g, 0.36 mole) was added to a suspension of sodium hydride (12.5 g, 0.5 mole) in toluene (300 ml.). The mixture was heated under reflux while isopropyl iodide (122 g 0.72 mole) in toluene (100 ml.) was slowly added. The mixture was then heated under reflux for a further 16 hours.

Ten percent hydrochloric acid (200 ml.) was added and the mixture was heated under reflux for 1 hour. The mixture was cooled and poured into water (1 liter). The organic layer was washed with NaHCO$_3$ solution, Na$_2$S$_2$O$_3$ solution and finally water, and then dried. The solvent was removed under reduced pressure and the residue was distilled to give 2-isopropyl-cycloheptanone, bp. 102-4°/25 mm. in 33% yield.

Magnesium (3.12 g, 0.13 mole), mercuric chloride (0.1 g) and dry tetrahydrofuran (10 ml) were stirred together. Chloromethylethyl ether (12.3 g, 0.13 mole) in tetrahydrofuran (15 ml) was then slowly added at −10° C. 2-Isopropylcycloheptanone (18.5 g, 0.12 mole) in tetrahydrofuran (25 ml) was added slowly keeping the mixture at −10°. This mixture was kept for 15 hours at −10° C. Saturated ammonium chloride solution (100 mls) and dilute ammonia (50 ml) were then added. The mixture was extracted with ether and the ether extracts dried and concentrated. The residue (11 g.) was distilled bp. 115/130°/12 mm Hg, mixed with formic acid (6.5 g) and heated at 100° C. for 2 hours. The solution was extracted with ether, washed with NaHCO$_3$ solution and dried (MgSO$_4$). The solvent was removed and the residue (11 g), silver oxide (16.2 g, 0.07 mole) and sodium hydroxide (2.8 g. 0.07 mole ) in water (150 ml) were stirred at 30° C. for 50 hours. The mixture was filtered and extracted with ether. The aqueous layer was acidified and extracted with ether. The ether was removed and the residue was distilled to give 2-isopropylcycloheptanecarboxylic acid, bp. 120°/0.2 mm.

Part B

2-Isopropylcycloheptanecarboxylic acid prepared as in Part A (3.5 g), thionyl chloride (15 ml) and carbon tetrachloride (15 ml.) were stirred at room temperature until reaction was completed. The acid chloride was distilled, bp. 60–2°/0.25 mm. 0.7 g. of the chloride thus prepared was added slowly to ethylamine (2.7 g) in ether (25 ml.). The mixture was washed with water and the ether layer dried (MgSO$_4$) and concentrated. The residue was recrystallised from 40°–60° C. petroleum ether, to give a crystalline product, mp. 75°–77° identified as N-ethyl-2-isopropylcycloheptanecarboxamide.

Analysis: Found C, 74.2; H, 11.9; N, 6.7; Calc. C, 73.9; H, 11.8; N, 6.6%.

EXAMPLE 27

Preparation of N,N-dimethyl-1-ethylcyclooctanecarboxamide

Part A

Sodium (3.7 g, 0.16 mole) was added to liquid ammonia (300 ml.) at 35° C. A catalytic amount of ferric nitrate was then added. After the solution had become grey in colour, ethyl bromide (17.4 g, 0.16 mole) and cyclooctyl cyanide (20.0 g, 0.14 mole) were added very slowly. The liquid ammonia was then allowed to evaporate over a period of 20 hours. Benzene and then water were added to the residue. The benzene layer was dried (MgSO$_4$) and distilled to give 1-ethylcyclooctyl cyanide, bp. 130–132°/17 mm.

The above cyanide (13 g., 0.07 mole) and 75% sulphuric acid (30 g.) were heated at 120° C. for 15 minutes. Sodium nitrite (20 g) was then added. The mixture was basified with 2N NaOH and extracted with ether. The aqueous layer was acidified and extracted with ether. The ether was removed and the residue was distilled to give 1-ethylcyclooctanecarboxylic acid, bp. 136–8°/1.8 mm.

Part B

1-Ethylcyclooctanecarbonyl chloride was prepared from the product of Part A by the method of Example 26, Part B. 1g. of the acid chloride in ether (10 ml.) was slowly added to a solution of dimethylamine (3.6 g.,) in ether (30 ml.). Water (50 ml.) was added and the ether layer was dried (MgSO$_4$) and concentrated. The residue was distilled to give N,N-dimethyl-1-ethylcyclooctanecarboxamide, bp. 113°/0.8 mm.

Analysis: C, 73.2; H, 12.0; N, 6.7; Calc. C, 73.9; H, 11.8; N, 6.6%.

EXAMPLE 28

Preparation of N-(1-ethylcyclooctanecarbonyl) glycine ethylester

Glycine ethyl ester hydrochloride (0.04 mole) and sodium bicarbonate (0.08 mole) were dissolved in water (50 ml.). 1-Ethylcyclooctanecarbonyl chloride (1 g. 0.04 mole) in ether (20 ml.) was then added with stirring. The other layer was separated, dried (MgSO$_4$) and concentrated. The residue was recrystallised from 40°-60° petroleum ether to give N-(1-ethylcyclooctanecarbonyl) glycine ethyl ester mp. 65°–7°

Analysis: C, 66.8; H, 10.3; N, 5.1; Calc: C, 66.8; H, 10.0; N, 5.2%.

EXAMPLE 29

Preparation of N,1-diisopropyl-2-methylcyclopentanecarboxamide

Part A

2-Isopropyl-2-carbethoxycyclopentanone was prepared by the method of Shive, Crouch, Lochte, J. Am. Chem. Soc. (1941) 63 2979.

Methylmagnesium iodide (0.22 mole) in ether (200 ml.) was added dropwise to a solution of 2-isopropyl-2-carbethoxycyclopentanone (40 g, 0.2 mole) in ether (150 ml.), and the mixture was heated under reflux for 17 hours. Dilute sulphuric acid was then added and the ether layer was separated and dried (MgSO$_4$). The ether was removed to leave 2-carbethoxy-1-methyl-2-isopropylcyclopentanol. This compound was dissolved in pyridine (200 ml.) and cooled to −10° C. Thionyl chloride (25 ml.) was then added keeping the temperature at −5° C. After 2 hours at −5° C., ether (500 ml) and an excess of 2N sulphuric acid were added and the organic layer was separated. The aqueous layer was extracted with ether and the combined extracts were dried (MgSO$_4$). The solvent was removed and the residue was distilled to give 1-carbethoxy-1-isopropyl-2-methylcyclopent-2-ene, bp. 107°–110°/17 mm.

A sample of the above olefin (20 g.) was hydrogenated (50 p.s.i.) in glacial acetic acid (120 ml.) in the presence of Adams catalyst (0.6 g.) for 24 hours at 25° C. The mixture was filtered, poured into an excess of 2H sodium hydroxide and extracted with ether. The extracts were dried (MgSO$_4$) and concentrated. The residue was distilled to give ethyl 1-isopropyl-2-methylcyclopentanecarboxylate bp. 102°–4°/15 mm.

The above ester (17.5 g. ), diethylene glycol (150 ml.) and sodium hydroxide (16 g.) were heated to 140° C. for 44 hours. The mixture was cooled and water was added. The mixture was extracted with ether and the aqueous layer was acidified. The aqueous layer was extracted with ether, dried (MgSO4) and the solvent removed. The residue was distilled to give 1-isopropyl-2-methyl-cyclopentanecarboxylic acid, bp. 94°–5°/0.4. mm.

Part B

The acid product of Part A was converted to the acid chloride by the method of Example 26, Part B. The acid chloride produced (1 g.) isopropylamine(2 g.) and ether (50 ml.) were stirred at room temperature for 18 hours. The mixture was washed with water and the ether layer was separated and dried (MgSO4). The solvent was removed and the residue was recrystalled from 40–60 petroleum ether to give N,1-diisopropyl-2-methylcyclopentanecarboxamide, mp. 90 5°–91.5° C.

Analysis: C, 72.8; H, 11.8; N, 6.2; Calc. C, 73.9; H, 11.8; N, 6.4%.

EXAMPLE 30

Preparation of N-(5-Hydroxy-n-pentyl)-1-isopropyl-2-methylcyclopentanecarboxamide 5-Amino-1- entanol (4 g.), 1-isopropyl-2-methylcyclopentanecarbonyl chloride (1 g.) and chloroform (100 ml.) were stirred at room temperature for 18 hours. The solution was washed successively with 2NHCL, 2N NaOH and water. The organic layer was dried (MgSO4) and distilled to give N-(5-hydroxy-n-pentyl)-1-isopropyl-2-methylcyclopentanecarboxamide bp, 162°/0.01 mm.

Analysis: C, 70.5; H, 11.7; N, 5.3; Calc: C, 70.6; H, 11.4; N, 5.5%.

EXAMPLE 31

Preparation of N-(1-ethyl-2-methylcycloheptanecarbonyl)-morpholine

1-Ethyl-2-methylcycloheptanecarbonyl chloride (1.5 g, 0.007 mole) in ether (10 ml.) was added slowly to a solution of morpholine (0.02 mole) in ether (10 ml.). The mixture was washed with dilute hydrochloric acid, dilute sodium bicarbonate and then with water. The other layer was dried and distilled to give N-(1-ethyl-2-methylcyclopheptanecarbonyl) morpholine bp. 145°–7°7°/0.35 mm.

Analysis: C, 71.6; H, 10.7; N, 5.6: Calc; C, 71.1; H, 10.7; N, 5.5%.

EXAMPLE 32

Preparation of N-(p-Methoxyphenyl)1-ethyl-2-methyl-cycloheptanecarboxamide

1-Ethyl-2-methylcycloheptanecarbonyl chloride (1.5 g, 0.007 mole) in ether (10 ml.) was added to a stirred solution of p-anisidine (0.01 mole) in ether (30 ml.). A further quantity of ether (100 ml.) was added and the solution was washed with dilute hydrochloric acid, dilute sodium hydroxide and then with water. The ether solution was dried (MgSO4) and the solvent was removed by distillation. The residue was recrystallised from 40–60 petroleum ether to give N-(p-Methoxyphenyl)-1-ethyl-2-methylcyclohexanecarboxamide, mp. 107°.

EXAMPLE 33

Preparation of N-(1',1'-dimethyl-2'-hydroxymethyl)-3,3,7-trimethylcycloheptanecarboxamide

Part A 3,3,7-Trimethylcycloheptanecarboxylic acid was prepared from 3,3,7-trimethylcycloheptanone (obtained from carvone, see E. J. Corey and H. J. Burke, J.A.C.S. (1955), 78, 174) by the method of Example 28, Part A.

Part B 3,3,7-Trimethylcycloheptanecarbonyl chloride, prepared from the product of Part A by the method of Example 26 Part B, (0.5 g. 0.0025 mole) in 10 ml methylene dichloride was added to a stirred solution of 2-amino-2,2-dimethylethanol (0.5 g) in 50 ml methylene dichloride. After 3 hours the solution was washed with 2N HCl, then with NaHCO3 solution and then dried (MgSO4). Removal of the solvent left an oil which was distilled to yield N-1', 1'-dimethyl-2'-hydroxyethyl)-3,3,7-trimethylcycloheptanecarboxamide, bp. 135°/0.015 mm.

Analysis: C 70.0; H 11.4; N 5.3.

Preparation of N,1,4,4-tetramethylcycloheptanecarboxamide

Part A 1,4,4-Trimethylcycloheptanecarboxylic acid was prepared from 3,3,7-trimethylcycloheptanol by the method of F. J. McQuillin and D. G. Parker, J. C. S. (Perkin I) (1974) 809.

Part B 1,4,4-Trimethylcycloheptanecarbonyl chloride, prepared from the product of Part A by the method of Example 26, Part B (0.5 g. 0.0025 mole) in 50 ml ether was added to a stirred solution of methylamine (excess) in water. After 2 hours the organic layer was separated, washed with 2N HCl and with NaHCO3 solution, and then dried.

Analysis: C 73.3; H 11.9; N 7.0; Calc: C 73.1; H 11.7; N 7.1%.

Other novel amides according to this invention including, for example, those listed hereinbefore in Table III, were prepared by analogous methods.

We claim:

1. In a consumer product for application to or consumption by the human body comprising a consumer product base and, as adjuvants in said base, (i) at least one of the following: a flavourant, colourant, perfuming agent, surface active agent or antiseptic agent, and (ii) an ingredient capable of stimulating the cold receptors of the nervous system of the surface tissues of the body in those parts of the human body with which the product comes in contact during use, the improvement which comprises using as the cold receptor stimulating ingredient an effective amount of a cold receptor stimulating alicyclic amide of the formula:

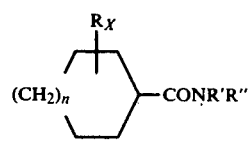

where
n is 0 or an integer of from 2-6 inclusive;
x has a value of 1, 2 or 3;
R is $C_1$-$C_5$ alkyl, at least one R group being in a 1, 2 or 3 position relative to the CONR'R" group and the total number of carbon atoms provided by the R groups and the carbocycle to which they are attached being from 8-14; and
R' and R" together represent a straight or branched chain alkylene group of up to 8 carbon atoms, the opposite ends of which group are joined to the nitrogen atom to form a 5- or 6-membered heterocycle, or a —$CH_2CH_2OCH_2CH_2$—group.

2. A product according to claim 1, wherein the cold receptor stimulating ingredient is of the formula:

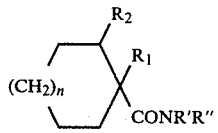

where
n is 0, 2 or 3;
at least one of $R_1$ and $R_2$ is $C_1$-$C_5$ alkyl and the other is H or $C_1$-$C_5$ alkyl; and
R' and R" together represent a straight or branched chain alkylene group of up to 8 carbon atoms, the opposite ends of which group are joined to the nitrogen atom to form a 5- or 6-membered heterocycle, or a —$CH_2CH_2OCH_2CH_2$—group.

3. A product according to claim 2, wherein the cold receptor stimulating ingredient is of the formula defined where one of $R_1$ and $R_2$ is a $C_3$-$C_5$ branched chain alkyl group having branching in an alpha position relative to the ring.

4. A product according to claim 1, which is a personal care product comprising a topically administrable base and, as adjuvants in said base, (i) a perfuming agent, a surface active agent or an antiseptic agent, and (ii) said cold receptor stimulant.

5. A product according to claim 1, which is a dentifrice comprising an orally acceptable dentifrice base and, as adjuvants therein, (i) a flavourant or antiseptic, and (ii) said cold receptor stimulant.

6. A product according to claim 1, which is a toilet lotion comprising an aqueous, alcoholic or aqueous alcoholic base and, as adjuvants therein, (i) an antiseptic, perfuming agent, colourant or a mixture thereof, and (ii) said cold receptor stimulant.

7. A product according to claim 1, which is a cosmetic preparation comprising an oil-in-water emulsion base, and, as adjuvants in said base, (i) at least one of the following: an antiseptic, perfuming agent or colourant and (ii) said cold receptor stimulant.

8. A product according to claim 1, which is a shaving preparation comprising a foamable base, containing a soap or synthetic surfactant and, as adjuvants in said base, (i) a perfume or antiseptic or a mixture thereof and (ii) said cold receptor stimulant.

9. A product according to claim 1, which is an edible preparation comprising an edible base and, as adjuvants in said base, (i) a flavourant and (ii) said cold receptor stimulant.

10. A product according to claim 1, which is a potable preparation comprising a potable base and, as adjuvants in said base, (i) a flavourant and (ii) said cold receptor stimulant.

11. A product according to claim 1, which is a chewing gum containing a chewing gum base and, as adjuvants therein, a flavourant and said cold receptor stimulant.

12. A method of stimulating the cold receptors of the nervous system of the human body which comprises applying thereto a composition as defined in claim 26.

13. In a tobacco or tobacco-containing manufacture comprising tobacco and an agent capable of stimulating the cold receptors of the nervous system of the nasal or oral mucosa when brought into contact therewith upon use of the manufacture, the improvement which comprises using as said agent an effective amount of a cold receptor stimulating amide of the formula:

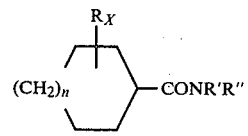

where
n is o or an integer of from 2-6 inclusive;
x has a value of 1, 2 or 3;
R is $C_1$-$C_5$ alkyl, at least one R group being in a 1, 2 or 3 position to the CONR'R" group and the total number of carbon atoms provided by the R groups and the carbocycle to which they are attached being from 8-14; and
R' and R" together represent a straight or branched chain alkylene group of up to 8 carbon atoms, the opposite ends of which group are joined to the nitrogen atom to form a 5- or 6-membered heterocycle, or a —$CH_2CH_2OCH_2CH_2$— group.

14. A manufacture according to claim 13, which is a cigarette containing said cold receptor stimulant.

15. A method of stimulating the cold receptors of the nervous system of the nasal and oral mucosa which comprises contacting said mucosa with an effective amount of a cold receptor stimulating amide entrained in a stream of tobacco smoke said amide being of the formula

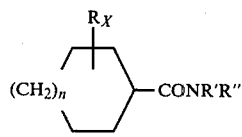

where
n is o or an integer of from 2-6 inclusive; x has a value of 1, 2 or 3;
R is $C_1$-$C_5$ alkyl, at least one R group being in a 1, 2 or 3 position relative to the CONR'R" group and the total number of carbon atoms provided by the R groups and the carbocycle to which they are attached being from 8-14; and
R' and R" together represent a straight or branched chain alkylene group of up to 8 carbon atoms, the opposite ends of which group are joined to the nitrogen atom to from a 5- or 6-membered heterocycle, or a —$CH_2CH_2OCH_2CH_2$— group.

* * * * *

UNITED STATES PATENT AND TRADEMARK OFFICE
CERTIFICATE OF CORRECTION

PATENT NO. : 4,318,900
DATED : March 9, 1982
INVENTOR(S) : David G. Rowsell et al.

It is certified that error appears in the above—identified patent and that said Letters Patent is hereby corrected as shown below:

In column 3, line 62, "confectionary" should read --confectionery--.

In column 6, line 39, "pounds" should read --pound--.

In column 6, line 42, "or" should read --are--.

In column 9, Table III, line 42, "N-(3',4'-dimethylphenyl)-2-iso-" should read --N-(3',4'-dimethylphenyl)-1-iso---.

In column 15, line 47, "propylcyclopentanecarbonyl peridine" should read --propylcyclopentanecarbonyl) piperidine--.

In column 17, line 33, "limitir;" should read --limiting;--.

In column 17, line 53, after "2-isopropyl-5-methyl" delete the second "methyl".

UNITED STATES PATENT AND TRADEMARK OFFICE
CERTIFICATE OF CORRECTION

PATENT NO. : 4,318,900

DATED : March 9, 1982

INVENTOR(S) : David G. Rowsell et al.

Page 2 of 3

It is certified that error appears in the above—identified patent and that said Letters Patent is hereby corrected as shown below:

In column 17, line 53, "alternatively" should read --(alternatively--.

In column 18, line 29, "cigarette." should read --cigarettes.--.

In column 18, line 66, "characteristics" should read --characteristic--.

In column 18, line 66, "me-" should read --men---.

In column 19, line 19, "characteristics" should read --characteristic--.

In column 22, line 25, "other" should read --ether--.

In column 22, line 60, "2H" should read --2N--.

In column 26, line 9, "claim 26" should read --claim 1--.

UNITED STATES PATENT AND TRADEMARK OFFICE
CERTIFICATE OF CORRECTION

PATENT NO. : 4,318,900

DATED : March 9, 1982

INVENTOR(S) : David G. Rowsell et al.

It is certified that error appears in the above—identified patent and that said Letters Patent is hereby corrected as shown below:

In column 26, line 29, after "or 3 position" add --relative--.

In column 26, line 64, "from" should read --form--.

Signed and Sealed this

Sixth Day of July 1982

[SEAL]

Attest:

GERALD J. MOSSINGHOFF

Attesting Officer

Commissioner of Patents and Trademarks